United States Patent [19]

Penniman

[11] Patent Number: 5,373,229
[45] Date of Patent: Dec. 13, 1994

[54] METHOD AND APPARATUS FOR MEASURING AN ELECTRICAL CHARACTERISTIC OF A FIBROUS DISPERSION

[75] Inventor: John G. Penniman, Carmel, N.Y.

[73] Assignee: Paper Chemistry Consulting Laboratory, Inc., Carmel, N.Y.

[21] Appl. No.: 703,560

[22] Filed: May 21, 1991

[30] Foreign Application Priority Data

May 21, 1990 [GB] United Kingdom ............... 9011333

[51] Int. Cl.⁵ ............................................ G01N 27/00
[52] U.S. Cl. .................................... 324/71.1; 162/263
[58] Field of Search ...................... 324/71.1; 73/53.03, 73/53.04; 162/198, 263

[56] References Cited

U.S. PATENT DOCUMENTS

| 3,186,215 | 6/1965 | Danforth | 73/53.04 |
| 4,253,329 | 3/1981 | Karnis | 73/53.03 |
| 4,535,285 | 8/1985 | Evans et al. | 324/71.1 |
| 4,687,986 | 8/1987 | Eriksson | 324/71.1 |

FOREIGN PATENT DOCUMENTS

| 3130529 | 2/1983 | Germany . |
| 262564 | 10/1986 | Germany . |
| 272508 | 10/1989 | Germany | 73/53.03 |
| WO86/00707 | 1/1986 | WIPO . |

OTHER PUBLICATIONS

Sack, Das Papier, Issue 30, No. 10A, 1976 pp. V42-43.

Primary Examiner—Hezron E. Williams
Assistant Examiner—Joseph W. Roskos

[57] ABSTRACT

A method for measuring a pressure dependent characteristic of a dispersion of a solid material in a fluid, comprising passing the fluid through a screen until a pad of the solid material is formed on the screen and, thereafter, measuring said characteristic, characterised in that the pressure on the screen side of the pad is maintained at a predetermined value, with respect to the pressure on the opposing side of the pad, during a measurement of the characteristic.

33 Claims, 3 Drawing Sheets

METHOD AND APPARATUS FOR MEASURING AN ELECTRICAL CHARACTERISTIC OF A FIBROUS DISPERSION

DESCRIPTION

The present invention relates to a method and apparatus for measuring an electrical characteristic of a fibrous dispersion. In particular, the present invention relates to a method and apparatus for measuring the streaming potential, or Zeta potential of feed stock, or furnish used in paper making machinery.

Zeta potential is an electrokinetic property of particles suspended in an aqueous medium containing charged ionic species and is an expression of the charge developed on or adjacent to such particles. It has been recognised that the Zeta potential of fibrous particles in the feed stock or furnish, used in paper making, has a considerable influence upon the paper produced therefrom. Zeta potential cannot be measured directly; however, it can be calculated from measurements of a related parameter known as streaming potential.

A general discussion of Zeta potential and its relevance to paper making is provided in "Electrokinetics in Paper Making—a position paper" by R. A. Stratton and J. W. Swanson in TAPPI, 64 No. 1, page 79–83 (1981). A survey of various methods of measuring Zeta potential, including those reliant upon measurements of streaming potential, is given in an article by H. J. Jacobasch et al. in Colloid and Polymer Science 263; 3–24 (1985).

From these references, it can be seen that the Zeta potential of feed stock or furnish, exiting the head box of a paper making machine, influences the quality of the paper produced by the machine, as a result of its significant effect during paper formation on the wire of the machine. It is known that, in principle, a high particle charge is necessary to ionically stabilize colloidal emulsions or dispersions. There is a mutual repulsion between charged particles of the same polarity, which keeps the particles apart and thereby imparts stability to an emulsion or dispersion system. Thus, stable dispersions of clay, calcium carbonate or titanium dioxide can have a charge or Zeta potential of $-50$ to $-60$ mV. or even higher. Pulp dispersions typically have a Zeta potential in the range of $-15$ to $-20$ mV. Cationic charge neutralizing chemicals such as alum, quaternary amines and wet strength resins, can reduce the Zeta potential of a paper making furnish to within the range of 0 to $-8$ mV. At these low values, the repulsive effect of the charge on the suspended particles is reduced to a negligible value and coagulation is maximised. Conversely, at higher Zeta potentials the degree of coagulation is reduced as the repulsive effect is increased. Thus, properties such as first pass retention, formation, drainage, white water consistency and strength can be optimized, for a particular type of paper, by adjusting the Zeta potential of its precursor furnish to an optimum.

A method and apparatus for determining streaming potential and hence calculating Zeta potential is disclosed in "Continuous measurement of the Streaming Potential on a paper machine" by W. Sack in DAS PAPIER 30, No. 10a, pp. V42–V46 (1976). A similar method and computer controlled apparatus is described in EP 0079726B (Wiggins Teape).

The device disclosed by Sack comprises a generally cylindrical cell, divided into two compartments by a sieve plate or filter mesh. The cell is provided with first and second fluid ports, arranged on either side of the sieve to allow fluid to be passed through the cell and sieve. An electrode is located in each compartment. Stock or furnish is pumped through the cell, flowing from the first port to the second port and a pad of particles from the furnish is built up on the sieve. The potential difference between the electrodes is measured when the pressure behind the building pad reaches a lower value and again when this pressure reaches a higher value. The streaming potential is taken from the difference between these measurements. After such a measuring cycle the first port is connected to a drain and fresh water is passed into the cell from the second port, to flush the pad out. Once flushed for 1–100 minutes, a further measurement may be taken. The apparatus is provided with a pressure sensor on the inlet port in order for the pressure difference across the pad to be determined. The accuracy of the results derived from this device and method are compromised by a number of factors. Firstly, the two electrical measurements are not made across the same thickness of pad. Secondly, only one measurement at each of the upper and lower pressure limits is made per operating cycle and, thirdly, the measuring cell is flushed with fresh water, upseting the equilibrium of the electrodes.

The measuring cell described in EP 0079726 is similar to that disclosed in the Sack paper. However, the operating cycle differs from that proposed by Sack, in that a pad of fibres is allowed to build up on the filter mesh to a full thickness, before any potential measurements are taken. Once the pad has been built up, the pressure across the pad is held, firstly, at a lower measured value and then at a raised measured value and finally, again, at the lower value. The potential difference between the electrodes is measured at both of said low pressure occasions and at said raised pressure occasion and a value for the streaming potential is then calculated from these measurements of pressure and streaming potential by a microprocessor. After such a measuring cycle has been completed, the cell is flushed with clean water. All the aforementioned operations are carried out under the control of a suitably programmed conventional microprocessor. The results and useability of this apparatus and method are compromised because the pad is only subjected to a raised pressure once during a measuring cycle and, also, because fresh water is used to flush out the cell between measuring cycles. The first of these features increases the margin for error in the calculated streaming potential and the second can lead to delays between measuring cycles, while the electrodes settle down before reuse. Another disadvantage of this apparatus stems from the fact that the pressure difference across the pad is measured using a pressure sensor in the pad side of the measuring cell. This pressure measurement is not and cannot be made at exactly the same time as the streaming potential is measured, because the control unit cannot accept data from two different sensors at one and the same time. Thus, if the pressure should fluctuate after the pressure has been measured, before or during measurement of the streaming potential, any such change will not be known and cannot be taken into account.

In both of the aforementioned sets of apparatus the electrodes extend into the measuring cells and, therefore, can hinder even pad formation and can hook up pad material which is being flushed from a cell.

In the methods disclosed in both the Sack paper and European Patent No. 0079726, the measured streaming potential is converted to Zeta potential using the Helmholtz Smoluchowski (H-S) equation, which is as follows:

Where h is viscosity; R=electrical resistance of the pad; S=streaming potential; T=temperature; E=a dielectric constant (of water); P=the difference between the raised and lowered pressures (The lower pressure is a nominal zero pressure); K=capillary geometry factor. In addition to the streaming potential and the difference between the raised and lowered pressure difference across the pad at which potential difference measurements are taken, the electrical resistance of the pad and the temperature are measured during an operating cycle and entered into the H-S equation for calculation of Zeta potential. The viscosity of the furnish, the dielectric constant of water and the capilliary geometry factor are considered to be constant.

In the method disclosed in European Patent No. 0079726 the Zeta potential is calculated by a microprocessor; whereas it is not disclosed in the Sack paper how the calculations are carried out.

It can be seen from the foregoing, that there is a requirement for a method and apparatus which allows substantially continuous and accurate monitoring of the Zeta potential of feed stock, or furnish. It is an object of the present invention to provide an improved method and apparatus for measuring an electrical characteristic, preferably the streaming potential, of a fibrous dispersion, particularly a feed stock or furnish used in paper making. It is a further object of the present invention to provide such a method, which can be operated substantially continuously, that is without undue delay between measuring cycles, with minimum operator attention.

According to a first aspect of the present invention, there is provided a method for measuring a pressure dependent characteristic of a dispersion of a solid material in a fluid, comprising passing the fluid through a screen until a pad of the solid material is formed on the screen and, thereafter, measuring said characteristic, characterised in that the pressure on the screen side of the pad is maintained at a predetermined value, with respect to the pressure on the opposing side of the pad, during a measurement of the characteristic. Thus, when the method of the first aspect of the invention is used, the pressure difference across the pad is automatically held at a predetermined and, hence, known value at the precise time when the pressure dependent characteristic is measured. Accordingly, when the measured characteristic and the pressure are used to calculate a further value, such as the Zeta potential, this further value is provided with greater accuracy than heretofor has been possible.

In a preferred embodiment the fluid is drawn through the screen to form the pad and, after the characteristic is measured, the pad is forced away from the screen by application of relatively increased or reduced pressure on the side of the screen which does not carry the pad. Preferably, the pressure on the screen side of the pad is maintained at at least two predetermined values, with respect to the pressure on the opposing side of the pad, and the characteristic is measured at both said at least two predetermined pressures.

According to a second aspect of the present invention there is provided a method of measuring a pressure dependent characteristic of a dispersion of a solid material in a fluid, comprising passing the fluid through a screen until a pad is formed on the screen, causing a pressure difference across the pad which repeatedly alternates between peak and trough values, determining the value of said electrical characteristic at each pressure peak and trough of a continuous series comprising at least three pressure peaks, commencing at a first pressure trough and ending with a final pressure trough, and, processing said values to provide an average, or final value of said characteristic. An advantage of this aspect of the present invention is that because the same pad is subjected to a plurality of pressure peaks at which measurements are taken, the final value of the electrical characteristic, determined from these measurements, is more accurate and consistent than a value obtained from measurements made at just one pressure peak.

In an embodiment, the first and second aspects of the invention are combined and, preferably, the measured characteristic is electrical and the solid is at least partially fibrous and the pad is formed from deposited fibers.

In a preferred embodiment, the values of the characteristic determined at the pressure peaks are each adjusted in response to an average of the values of the characteristic, determined at the immediately preceding and following pressure, troughs and the resulting adjusted values are processed to provide the final value of the characteristic. An advantage of this embodiment is that it further enhances the accuracy of the results obtained.

Preferably, the mean of the values of said characteristic determined at each pair of said immediately preceding and following pressure troughs is subtracted from the value of said characteristic determined at each intermediate pressure peak, to provide an adjusted value corresponding to each pressure peak and said adjusted values are processed to provide the final value of the characteristic. Said processing can comprise an averaging process; for example, for a series of n adjusted values, where n is an odd number, the $(n-1)/2$ greatest values and the $(n-1)/2$ smallest values of the characteristic are discarded to leave the median value to serve as the final value of the characteristic. More preferably, the final result is rejected if the difference between the values of the characteristic at the first and last pressure troughs in the complete series exceeds a predetermined value.

In a further preferred embodiment the screen is located in a cell and divides the cell into first and second chambers, the fluid is passed into the cell, entering the first chamber and passing into the second chamber, until the pad is formed in the first chamber between first and second electrodes, fluid which has passed through the screen being accommodated in the second chamber, and, after the characteristic has been measured, fluid from the second chamber is forced back through the screen and the first chamber to flush the pad from the screen and out of the cell. An advantage of this embodiment is that, because the electrodes are not exposed to fresh water during flushing, their equilibrium is not disturbed and a second measuring cycle can follow immediately after the pad from a first has been flushed from the cell, without compromising the measurements obtained in the second cycle.

In a further preferred embodiment the measured electrical characteristic is the streaming potential, which is determined from measurements of the potential difference between the first and second electrodes, which are located on screen and opposed sides of the pad respectively. The pad conductance and the temperature of the fluid can be determined during the measurement cycle, preferably during a pressure trough and most preferably during the last pressure trough. In a most preferred embodiment, the Zeta potential is determined from measurements of the dispersion's temperature, pad conductance and streaming potential.

In a third aspect, the present invention relates to apparatus for measuring a pressure dependent characteristic of a dispersion of a solid material in a fluid, comprising means for passing the fluid through a screen for forming a pad of the solid material on the screen and means for measuring said characteristic, characterised by further comprising pressure regulating means for maintaining the pressure on the screen side of the pad at a predetermined value, with respect to the pressure on the opposing side of the pad, during measurement of the characteristic. When used in carrying out a method in accordance with the first aspect of the present invention, apparatus in accordance with the second aspect of the invention provides the advantages discussed above in connection with the first aspect of the invention.

In an embodiment of the third aspect of the invention the apparatus comprises a cell divided into first and second chambers by the screen, arranged for allowing the dispersion to enter the first chamber and a portion of the liquid to pass through the screen into the second chamber, leaving the pad of solid material on the screen, characterised in that the pressure regulating means are arranged to maintain the pressure in the second chamber at the predetermined value, with respect to the pressure in the first chamber, during measurement of the characteristic. Preferably the pressure regulating means are arranged to maintain the pressure in the second chamber at two or more predetermined values with respect to the pressure in the first chamber.

In a fourth aspect the present invention provides apparatus for use in measuring an electrical characteristic of a dispersion of a solid material in a fluid, comprising a cell divided into first and second chambers by a screen, arranged for allowing the dispersion to enter the first chamber and a portion of the liquid to pass through the screen and into the second chamber, leaving a pad of the solid material on the screen, and at least one electrode for measuring said characteristic, characterised in that the electrode is substantially flush with the wall of the first chamber. An advantage of this aspect of the invention is that the electrode does not hinder even pad formation and that, when the pad is removed, it will not become hooked upon the electrode.

In a preferred embodiment of this aspect of the invention, the electrode is in the form of a ring or annulus and, as such, provides an even and consistent signal from around the pad.

In embodiments of any aspect of the invention, the first and second electrodes are located in the first chamber, the first electrode is embodied by the screen, or is located immediately adjacent to the screen and the second electrode is spaced away from the screen. Preferably, a computer control means is programmed to carry out the method of the first or second aspect of the invention and to process measured values of the electrical characteristic in order to provide a final value thereof. A more preferred form of the apparatus includes means for measuring the temperature of fluid passing into the cell and means for measuring the conductivity of a pad formed between the electrodes. The computer control means can be programmed to calculate Zeta potential from streaming potential values, pressures known from the pressure regulating means and temperatures and conductivity values derived from the aforesaid means. The computer means is preferably an IBM or IBM compatible personal computer system and, preferably includes a monitor for displaying measured and calculated values.

Further preferred embodiments and features of the various aspects of the present invention are described in the sub-claims included herewith. The various features of the different aspects of this invention may be combined at will, to provide additional embodiments of the invention, which may not be set out in the foregoing description but which, nevertheless, are considered to be within the scope of the invention.

A particular embodiment of the present invention will now be described by way of example only, with reference to the following drawings.

Figure 1:
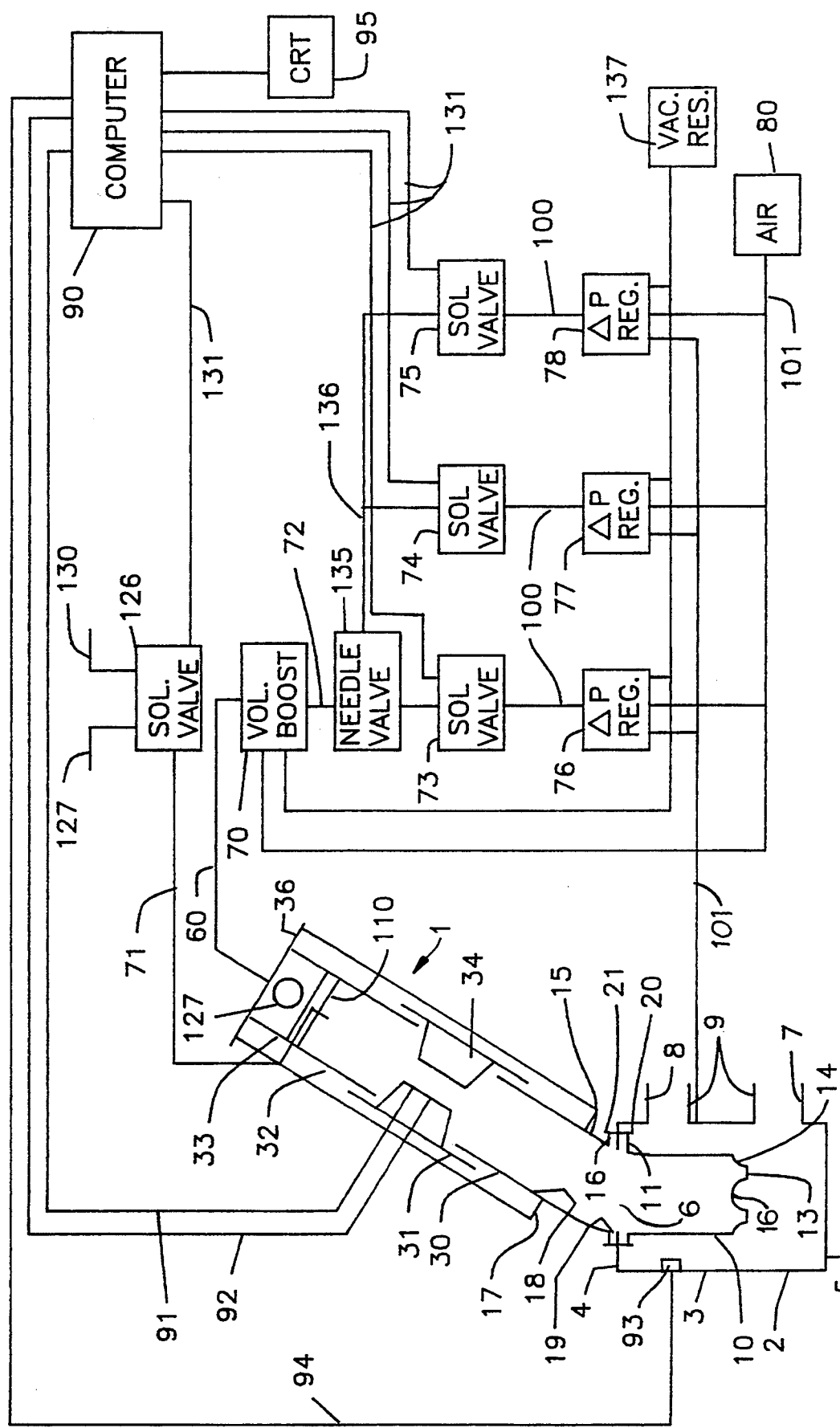
FIG. 1 is a block diagram of apparatus in accordance with the present invention.

The apparatus will be described, firstly, with reference to FIG. 1. In FIG. 1 the "wet-end" components of the apparatus are shown in cross-section, whereas the "dry-end" or controlling components are represented schematically. In practice, the dry-end components are located in a cabinet, or cabinets remote from the "wet-end" components.

The wet-end components include a substantially cyclindrical and hollow measuring cell 1 and a substantially cylindrical and hollow vessel 2. The vessel 2 comprises a circular cross-sectioned sleeve 3 extending between first and second end plates 4 and 5. The first end plate 4 defines a centrally located orifice 6. A furnish inlet 7 is defined in the sleeve 3, adjacent to the second end plate 5 and a furnish outlet 8 is defined through the sleeve 3, adjacent to the first end plate 4. Both the inlet 7 and the outlet 8 include radially outwardly extending tubular members 9 for engagement with furnish conduits leading to, or from a paper making machine.

An intake tube 10 extends inside the vessel 2 from the first end plate 4 towards the second end plate 5. An annular flange 11 extends radially outwardly from a first end part 12 of the intake tube 10 and is fixed in abutment with the radially innermost portion of the first end plate 4, surrounding the orifice 6. A second end part 13 of the intake tube 10 opens into the vessel 2, at a location between the furnish inlet 7 and outlet 8. Four semi-circular reliefs 14 are defined by diametrically opposed portions of the second end part of the tube 13. The reliefs 14 extend into the wall of the intake tube 10, from its otherwise plannar and annular faced second end part 13, partway towards its first end part 12.

First and second annular flanges 16 and 17 extend radially outwardly from first and second opening defining end parts 18 and 19 of an elbow tube 15. The first annular flange 16 of the elbow 15 is held in engagement with the radially inner edge portion of the first end plate 4 of the vessel 2, surrounding the orifice 6 with the tubular elbow 15 extending away from the vessel 2. A plurality of registering holes are formed through the first elbow flange 16, annular flange 11 and the radially inner edge portion of the first end plate 4. Conventional bolts 20 extend through said registering holes and nuts 21 are threadably engaged upon the bolts 20 and tightened thereto, clamping the assembly of annular flange 11, first elbow flange 16 and end plate 4 in tight sealing engagement, about the orifice 6. In an alternative embodiment, a straight parallel sided tube is substituted for the elbow tube 15, so that the cell 1 stands upright on the vessel 2.

Figure 2:
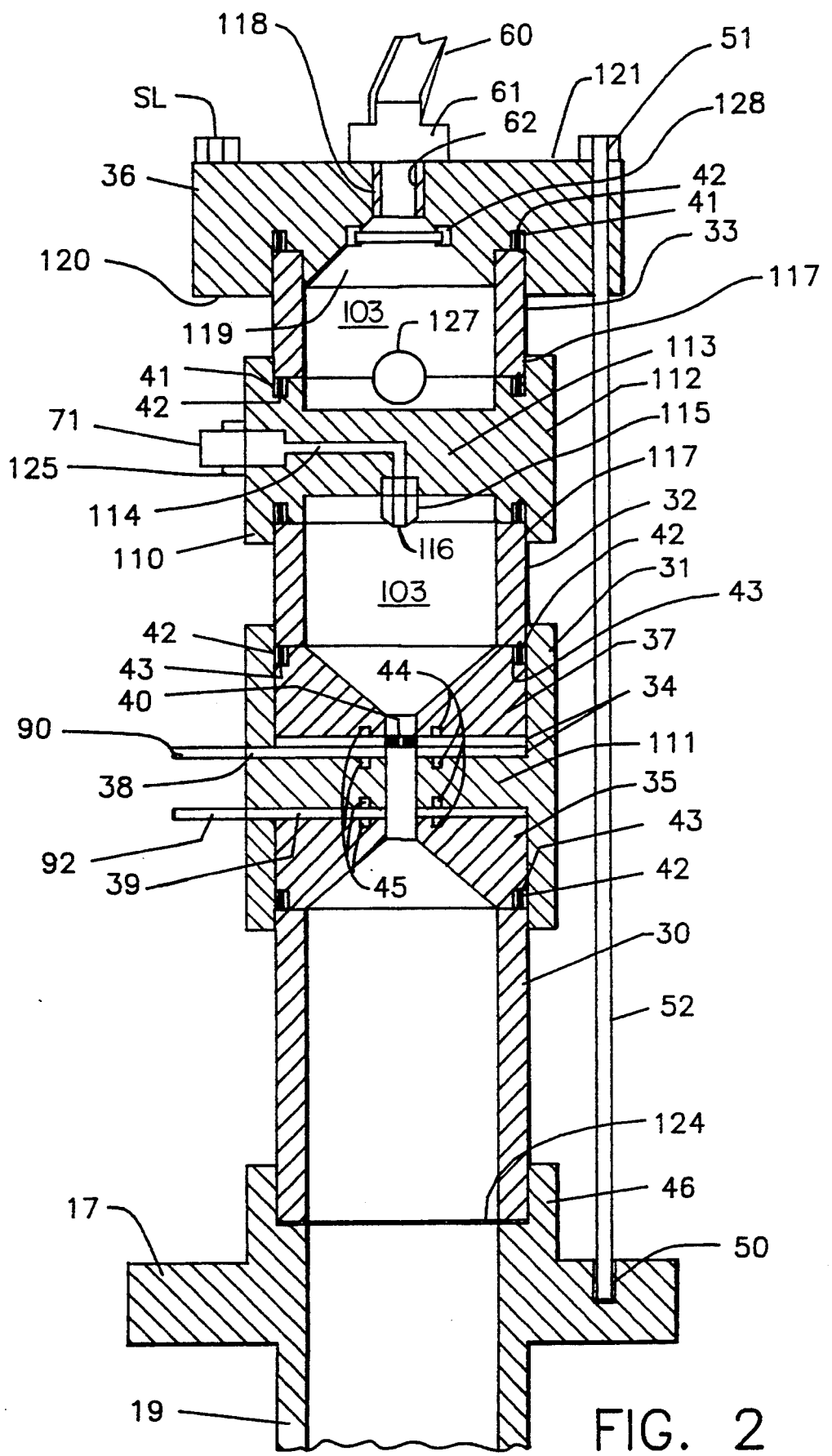
FIG. 2 is a partial cross-section of a measuring cell.

The measuring cell 1 is shown in detail in FIG. 2 and will now be described with reference thereto. All the components of the cell 1 are formed from an electrically insulating plastics resin material, such as polymethylmethacrylate, unless otherwise stated. The measuring cell 1 comprises first, second, third and fourth tubular body members 30, 31, 32 and 33 an end cap 36, a screen and electrode assembly 34 and a nozzle assembly 110. The first, third and fourth tubular body members 30, 32 and 33 have the same inner and outer diameters. The second tubular body member 31 is integrally formed with an internal annular restriction 111, midway between its open ends and is otherwise dimensioned to be a sliding fit over the first and third tubular body members 30 and 32. The screen and electrode assembly 34 comprises first and second annulae 35 and 37. The first and second annulae 35 and 37 are similar, being substantially right angled triangular in cross section. The radially outermost surfaces of the annulae 35 and 37 are of the same diameter as the outer surfaces of the first and third tubular body members 30 and 32 and, thus are a sliding fit within the second tubular body member 31. The radially innermost portions of the annulae 35 and 37 are of the same reduced diameter as the inner margin of the annular restriction 111.

The cell 1 is assembled with the annulae 35 and 37 located coaxially within the second tubular body member 31, with the annular restriction 111 sandwiched between the larger radially extending faces of the first and second annulae 35 and 37. The assembly of the first and second annulae 35 and 37 and the annular restriction 111 provides a choke within the second tubular body member 31. First and second annular electrodes 38 and 39, formed from an electrically conductive metal, are sandwiched between, respectively, the first annulus 35 and the annular restriction 111, and the annular restriction 111 and third annulus 37. The electrodes have the same outer diameter as the annulae 35 and 37 but their inner diameter is marginally less than that of the annulae 35 and 37 and the annular restriction 111 such that, when assembled as aforesaid, the electrodes extend radially inwardly into the choke defined by the annulae 35 and 37 and the annular restriction 111. A disc shaped perforated screen 40 is sandwiched between the first electrode 38 and the first annulus 35. The first and third tubular body members 30 and 32 are telescopically engaged within the second tubular body member 31, on either side of the filter and electrode assembly 34. The first tubular body member 30 is in abutment with the first annulus 35 and the third tubular body member 32 is in abutment with the second annulus 37. Rubber O-rings 42 are located in annular grooves 43 formed in the radial peripheries of the first and second annulae 35 and 37. The annular groove 43, formed in the first annulus 35, is located such that the O-ring 42, located therein, is in fluid tight sealing contact with the first annulus 35, the first tubular body member 30 and the second tubular body member 31. The annular groove 43, formed in the second annulus 37, is similarly located such that the O-ring 42, located therein, is in fluid tight sealing contact with the second annulus 37, the third tubular body member 32 and the second tubular body member 31. Likewise, smaller annular channels 44 are formed in the facing surfaces of the radially inner margins of the annulae 35 and 37 and the annular restriction 111. Smaller O-rings 44 are located within said channels 43 and provide a fluid tight seal between abutting annulae, 35 and 37, the annular restriction 111, the screen 40 and the electrodes 38 and 39.

The nozzle assembly 110 comprises an annular sleeve portion 112 with a single spoke member 113, extending diametrically across and within the sleeve portion 112. A passage 114 extends from the radial periphery of the sleeve portion 112, through the sleeve portion 112 and along the spoke member 114, to a nozzle 115, which defines an axially facing outlet 116. Radially inwardly facing annular steps 117 are defined in the axial entermities of the sleeve portion 112 and are dimensional to provide seats for the third and fourth tubular body members 32 and 33. The nozzle assembly 110 is fitted onto the third tubular body member 32 with the end of the latter, which is remote from the screen and electrode assembly, snuggly seated in one of the steps 117 such that the nozzle outlet 116 faces the screen 40. The fourth body member is seated in the other step 117 and extends coaxially with the first, second and third body members 30, 31 and 32, away from the nozzle assembly 110. The end cap 36 is circular in plan and defines a centrally located passage 63 extending axially therethrough. The passage 63 is defined by a frusto-conical surface 119, extending from the end cap's otherwise plannar first face 120, and a threaded cylindrical surface 118 extending from the narrow end of the frusto-croncial surface 119 to the second substantially plannar face 121 of the end cap 36. A rectangular sectioned annular channel 123 is formed in the first face 120 and surrounds the opening of the passage 63. The rectangular sectioned annular channel 123 is dimensioned so as to be a snug fit over an open end of the fourth tubular body member 33. At its widest, where it opens out of the end cap 36, the passage 63 has substantially the same diameter as the inner diameter of the fourth body member 33. The end cap 36 is fitted onto the open end part of the fourth body member 33, remote from nozzle assembly 110, with said open end part seated in the square sectioned annular channel 123.

One of a plurality of narrow annular channels 41 is formed in each of the annular faces, defined within the steps 117 and the rectangular sectioned annular channel 123, which are in abuttment with the annular end faces of the third and fourth tubular body members 32 and 33. Further Rubber 0 rings 42 are located in the narrow annular channels 41 and provide fluid tight seals between the end cap 36, fourth body member 33, nozzle assembly 110 and the third body member 32.

The end part of the first tubular member 32, remote from the second tubular member 31, is in sealing engagement with the second annular elbow flange 17, within the confines of an annular upstand 46 which is formed on the second annular elbow flange 17. A gasket 124 is sandwiched between the tubular member 32 and the second elbow flange 17, in order to maintain a fluid tight seal between the third tubular body member 32 and the second elbow flange 17. The second annular elbow flange 17 and the end cap 36 have substantially the same diameter, which is greater than the diameter of the other cell components. Three equally spaced threaded holes 50 (only one of which is shown) are formed through the second annular elbow flange 17 and three equally spaced smooth bored holes 51 are formed through the end cap 36. All of the holes 50 and 51 are disposed on circular arcs of greater diameter than the outer diameter of the second tubular body member 31 and nozzle assembly 110. Bolts 52 extend through the smooth bored holes 51 and are threadably engaged in the threaded holes 50. The bolts 52 are tightened until their heads abut the second face of the end cap 36 and act to hold all the components of the cell 1 in sealing engagement with one another in the aforementioned manner.

A spherical float 127 is located in an upper chamber 103, defined within the cell 1 by the screen 34, the second annulus 37, the third and fourth tubular body members 32 and 33, the nozzle assembly 110 and the end cap 36. The spherical float 127 is dimensioned so that it cannot pass through the gaps in the nozzle assembly 110 between the sleeve portion 112 and the spoke member 114 and is trapped in the chamber 103, between the nozzle assembly 110 and the end cap 36. A rubber gland 128 is accommdated in an annular grove formed in the narrower margin the the frusto-conical surface 119 and around the entrance to the narrow part of the passage 63, defined by the threaded surface 118. The spherical float 127 has a diameter greater than the opening through the gland 128.

A flexible air hose 60 is frictionally engaged over a ferrule 61. The ferrule 61 carries an outwardly facing screw threaded portion 62, extending beyond the air hose 60, which is threadably engaged in the screw threaded portion of the passage 63. Similarly, a flexible waterhose 71 is frictionally engaged over a second screw threaded ferrule 125. The ferrule 125 is threadably engaged in a corresponding thread in the passage 114, where the latter opens out of the radical periphery of the sleeve portion 112 of the nozzle assembly 110.

Electrically conducting wires 91 and 92 extend through and are frictionally engaged in radially extending passages defined in the second tubular body member 31 and are held in electrical contact with the radially outer peripheries of the electrodes 38 and 39.

Referring back to FIG. 1, the flexible hoses 60 and 71 are shown schematically, extending from a simplified representation of the measuring cell 1. The air hose 60 is connected to a volume booster 70. The volumn booster 70 is connected to a needle valve 135 via a pneumatic hose 72. A branched pneumatic hose 136 connects the needle valve 135 to first, second, and third solenoid actuated valves 73, 74 and 75. The first, second, and third solenoid actuated valves 73, 74 and 75 are, respectively, connected by pneumatic hoses 100 to first, second and third differential pressure regulators 76, 77 and 78. The differential pressure regulators 76, 77 and 78 are connected by pneumatic hoses 101 to the inside of the vessel 2, to a source of compressed air 80 and to a vacuum reservoir 137. The first differential pressure regulator 76 is set to impose a pressure equal to 1.5 PSI below that in the vessel 2 at its output to the second solenoid valve 73. The pressures imposed by the second and third differential pressure regulators, at their outputs, are respectively 8 PSI below and 6 PSI above the pressure within the vessel 2.

The volume booster 70 allows compressed air from the source 80 to flow into the air hose 60, or connects the vacuum reservoir 137 to the air hose 60, and maintains the pressure of the air flowing in air hose 60 substantially equal to the pressure imposed upon the volume booster 70 through the needle valve 135. Very little air flows between any of the pressure regulators 76, 77 and 78 and the volume booster 70; air in the interconnecting pneumatic hoses 72, 136 and 100 is moved by a pressure regulator 76, 77 or 78 just enough for it to impose its aforementioned output pressure on the volume booster 70 and only when connected thereto by its associated solenoid valve 73, 74 or 75.

The needle valve 135, being a restriction of variable size in the pneumatic hoses 72 and 136, provides a variable rate damper to any air flow between the pressure regulators 76, 77 and 78 and the volume booster 70. The needle valve 135, should be adjusted so as to resist the transmission of any "switch on" pressure wave from the solenoid valve 73, 74 or 75 to the volume booster 70 and to thereby prevent a momentarily exaggerated pressure signal from reaching the volume booster 70. The restriction provided by the needle valve, however, should not be so great that it prevents sufficient air from flowing, for the substantially immediate transmission of a pressure signal from a pressure regulator 76, 77 or 78 to the volume booster 70. The water hose 71 is connected to a fourth solenoid actuated valve 126 which, in turn, is connected to a supply of filtered white water 130 or a fresh water supply 127.

A control computer 90 is connected by cables 131 to the first, second, third, and fourth solenoid valves 73, 74 and 75 and 126 for sending actuating signals thereto. The control computer 90 receives signals from the electrodes 38 and 39, along wires 91 and 92 and temperature data, from a temperature sensor 93 along a cable 94. The computer transmits data to a display screen 95.

In use stock or furnish from a paper making machine is pumped through the vessel 2, entering through the inlet 7 and leaving through the oulet 8. The furnish pressure in the vessel 2 should be regulated to between 0 and 75 PSI. The computer 90 is programmed to instruct the remaining components of the apparatus to carry out the measuring cycle depicted in FIG. 3 and as follows.

Step 1

The first and third solenoid valves 73 and 75 are held shut and the second solenoid valve 74 is opened. Thus, the second differential pressure regulator 77, acting through the second solenoid valve 74, imposes a pressure signal on the volume booster 70, via hoses 72 and 136 and the needle valve 135, which is 8 PSI below that of the furnish within the vessel 2. The volume booster 70 then withdraws air from the cell 1 along airhose 60, by maintaining a pressure 8 PSI below that of the furnish in the airhose 60. Thus, furnish is sucked into the intake tube 10, through its second end 13 and flows into the cell 1. The apparatus is held in this condition for 20 seconds whilst a pad of fibres builds up on the filter screen 34, filling the space between the electrodes 38 and 39. This period, called the "fill time", is pre-set by the operator and is chosen after experimentation to be of sufficient duration to allow the pad to build up to completely fill the space between the electrodes 38 and 39. This pad building period is shown at A in FIG. 3. Furnish which has passed through the screen 34 collects in the upper chamber 103.

Step 2

The first solenoid valve 73 is opened and the second solenoid valve 74 closed, thus causing the volume booster 70 to impose a pressure in the upper chamber 103 of the measuring cell 1 of 1½ PSI below that of the furnish in the vessel 2. The apparatus is held in this "first pressure" trough condition for about 2 seconds while the control computer 90 reads and stores a first value of the potential difference between the electrodes 38 and 39. This first pressure trough is shown at $B_1$, in FIG. 3.

Step 3

The first solenoid valve 73 is then closed and the second solenoid valve 74 is opened, thus causing the volume booster 70 to reimpose a pressure in the upper chamber of the measuring cell of 8 PSI below that of the furnish in the vessel 2. The apparatus is held in this "first pressure peak" condition for about 2 seconds, while the control computer reads and stores a second valve of the potential difference between the electrodes 38 and 39. This first pressure peak is shown at $A_1$, in FIG. 3.

Figure 3:
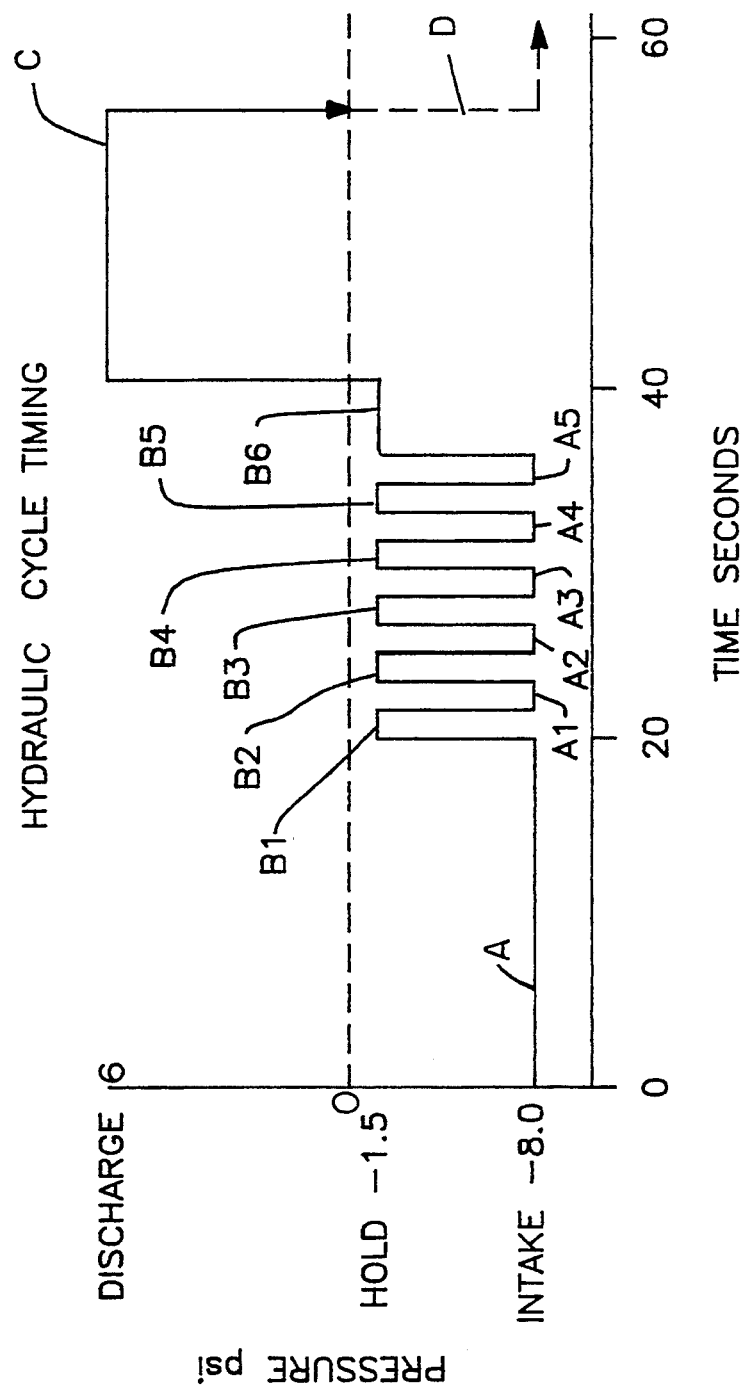
FIG. 3 is a plot of pressure across the pad against time, showing an operating cycle for the apparatus shown in FIG. 1.

Steps 2 and 3 are then repeated 4 times as shown at $B_2$-$B_5$ and $A_2$-$A_5$ in FIG. 3. The control computer 90 reads and stores a value of the potential difference between the electrodes 38 and 34 at each repetition of steps 2 and 3, i.e. at each of the pressure peaks $A_2$-$A_5$, and pressure troughs $B_2$-$B_5$.

Step 4

After the final repetition of Step 3, at $A_5$, the control computer 90 causes the apparatus to carry out a final repeat of Step 2 ($B_6$ in FIG. 3), in which the apparatus is held in a pressure trough condition for 5–10 seconds; during which the potential difference between the electrodes 38 and 39 is read and stored by the computer 90, the conductivity (resistance) of the fibre pad is read (via the electrodes 38 and 39) and stored by the computer 90, and the temperature of the furnish is recorded from the temperature sensor 93 and stored by the computer 90.

Step 5

Both the first and second solenoid valves 73 and 74 are then held shut and the third solenoid valve 75 is opened, thus causing the volume booster 70 to impose a pressure in the upper chamber of the measuring cell 1 of 6 PSI above that of the furnish in the vessel 2. The apparatus is held in this flushing condition, C in FIG. 3, for about 15 seconds, while the furnish which had collected in the upper chamber 103 of the cell is forced out of the cell 1, via the filter screen 34 and intake tube 10, by compressed air from the source 80 which is directed into the air hose 60 by the volume booster 70. As the furnish is passed out of the cell 1, it carries the pad away from the screen 34, out of the cell 1, through the intake tube 10 and into the vessel 2. The remains of the pad is then carried out of the vessel 2 through the furnish outlet 8.

Steps 1–5 then may be repeated as many times as desired. The beginning of a second cycle of Steps 1–5 is shown by the broken line D in FIG. 3.

Since the pressure across the pad during the pressure troughs $B_1$-$B_6$ in FIG. 3 is very low, at 1.5 PSI, the potential difference between the electrodes 38 and 39 measured in the troughs is an expression of the Assymmetry potential (See Hunter and Alexander, Journal of Colloid Science 17, 781–788 (1962)).

After a measuring cycle of Steps 1–5, the control computer 90 then compares the difference between the potential difference measured at $B_1$ in FIG. 3 and that measured at $B_6$ in FIG. 3. If this difference exceeds a predetermined value, which may be set before the apparatus is used, the control computer 90 rejects all the data stored in that particular cycle of Steps 1–5. Thus, data gathered during a period when the Assymmetry Potential has fluctuated to an unacceptable extent is rejected. If, however, the difference between the potential difference measurement at $B_1$ and $B_6$ in FIG. 3 is below such a predetermined value, the control computer 90 will proceed to calculate and output to the display screen 95 a value for the streaming potential which has been corrected to take the fluctuating Assymmetry potential into account. Firstly, the mean of the potential difference values measured at the pressure troughs immediately preceding and following each pressure peak is subtracted from the potential difference measured at that peak (for example the mean of the potential differences measured at $B_1$ and $B_2$ (in FIG. 3) is subtracted from the potential difference at $A_1$ and the mean of the potential differences measured at $B_2$ and $B_3$ is subtracted from the potential difference at A etc.) to provide a series of five corrected Streaming potential values. The two largest and the two smallest values in this series are then discarded and the remaining, intermediate or median value is retained as the final value for use in calculating the Zeta potential. Thus one value for the Streaming potential is provided per cycle of Steps 1–5.

The Zeta potential is then calculated by the control computer 90 using software equating to the Helmholtz-Smoluchowski equation, as hereinbefore set out. The viscosity, dielectric constant and capillary geometrey factor are constant, known parameters which are programmed into the control computer 90. The value for the streaming potential is that previously determined as set out above and the values for the electrical resistance (conductivity) of the pad and temperature of the furnish are those measured at $B_6$ in FIG. 3. The pressure difference is known at 6.5 PSI, and is the difference between the pressures imposed in the upper chamber 103 of the measuring cell 1, with respect to that in the vessel 2, by the volume booster 70 under the control of the first and second differential pressure regulators 76 and 77. This arrangement obviates any need to measure the pressure in any part of the cell. Again, as with the streaming potential, a single value for the Zeta potential is displayed on the display screen 95, for each cycle of Steps 1–5.

The control computer 90 is programmed to allow an operator to enter altered values for the viscosity, dielectric constant, and capillary geometrey factor, if appropriate. Futhermore, the length and number of pressure peaks and troughs and the fill time may also be adjusted through the control computer 90, which, in addition to processing the data derived from the measuring cell 1, also controls all the operations of the solenoid values 73, 74 and 75. Furnish consistencies of between 0.1% and 6% may be accommodated by altering the fill time; the greater the consistency, the shorter the fill time required to build a pad.

Whenever the cell 1 requires cleaning of accumulated debris, the first valve 70 is closed and the fifth valve 126 opened to either the filtered white water supply 130 or the fresh water supply 127, allowing white or fresh water to enter the chamber 103, via the hose 71 passage 114 and nozzle 115. Since the nozzle opening 116 faces the screen 40, a cleaning jet of white or fresh water is caused to impinge upon the screen and the walls of the chamber 103. When the level of fluid in the upper chamber 103 rises above the nozzle assembly 110, the spherical float 127 is caused to rise up towards the end cap 36. Once the chamber 103 becomes substantially filled with fluid, the float 127 comes into sealing engagement with the gland 128, preventing fluid from entering the dry end of the apparatus, through the airhose 60, and damaging any components such as the volume booster 70.

The control computer 90 maybe programmed to calculate and display a "Confidence Factor", intended to provide an estimate of a level of confidence that may be placed in the accuracy and reproducibility of the Zeta Potential Data. The Confidence Factor is calculated from the greatest and least values for the difference between the potential difference measured at $B_1$ in FIG. 3 and that measured at $B_6$ at FIG. 3, after a number of cycles of steps 1–5. The least value is divided by the greatest value and the result is multiplied by 10 to provide the Confidence Factor.

The apparatus may include dedicated vacuum and compressed air pumps for providing the compressed air source 80, or to supply the vacuum reservoir 137. When so configured, apparatus in accordance with the present invention is easily transportable and can be quickly installed to work off, for example, a headbox by-pass line.

In a preferred form of the described cell 1, the exposed area of screen 34 has a diameter of half an inch; whereas the internal diameter of the first and third tubular body members 30 and 32 is two inches. Accordingly, as a result of this sixteen times reduction in cross sectional area, full pad formation is achieved after the passage of one sixteenth of the amount of furnish that a full width screen 40 would require. This is especially advantagous when measuring low consistency furnishes, such as those used in the manufacture of tissue, which typically have a consistency of 0.2%. Furthermore, a small diameter screen is inherently more rigid in use and, therefore, provides results of greater accuracy.

Optionally, a fine gauze formed from woven nylon threads can be installed between the first electrode 38 and the screen 40. The use of such a gauze can be an advantage when the furnish being measured has a high clay content, since without the imposition of the gauze, the screen can easily become clogged with clay which is not readily dislodged between measuring cycles. The mesh of the gauze is selected to minimize any clogging and, in some circumstances two gauzes of different mesh size can be layed over each other, between the first electrode and the screen 40. Typically, the mesh size of the gauze is between 5 $\mu$m and 200 $\mu$m and, for example, when bentonite clay is present in the furnish, a gauze having a 20 $\mu$m mesh is perferably used.

The control computer 90 may be programmed for separate use with a plurality of different cells 1. When so programmed, the control computer 90 requires the operator to enter a chamber constant to compensate for small differences between different cells 1. The chamber constant for a cell 1 is obtained by filling the cell 1 with a solution of known conductivity, and measuring the conductance across the electrodes 38 and 39. The conductivity should be divided by the measured conductance to provide the chamber constant.

The signal from the electrodes 38 and 39 is weak and, thus, it is preferred that the control computer 90 is located close to the cell 1, in order to keep the lengths of the cables 91 and 92 as short as possible, i.e. below 6 meters in length. This expedient avoids the need for a head amplifier on the cell 1. If several cells 1 are installed on a large paper making plant, it is preferred that each cell 1 is provided with a dedicated control computer 90 and set of dry end components. In these circumstances, the control computers 90 are networked together and forward their outputs to a master computer in place of display screens 95. The master computer then displays or further processes these outputs onto a single screen.

The length of an operated cycle is dependant on the operator entered fill time, but is usually less than one minute. It is not always necessary for measurements to be taken so frequently in practice. Acccordingly, the control computer 90 maybe programmed to introduce a user selected pause between the measurement cycles of up to ten minutes or more.

The control computer may be programmed to carry out a number of statistical analyses on the raw data. For example the software may be configured to calculate a trailing average from 2 to 10 data points, to smooth out aberrations and generate a smooth data plot.

I claim:

1. A method for measuring a pressure dependent characteristic of a dispersion of a solid material in a fluid, said method comprising passing the fluid through a screen located within a cell and thereby dividing said cell into first and second chambers, wherein the fluid is passed into the cell, entering the first chamber and thereafter passing into the second chamber, until the pad is formed in the first chamber between first and second electrodes, and thereafter measuring said characteristic, wherein the pressure on the screen side of the pad is maintained at a predetermined value with respect to the pressure on the opposing side of the pad during measurement of said characteristic, and, after the characteristic has been measured, forcing fluid from the second chamber back through the screen and the first chamber, to flush the pad from the screen out of the cell.

2. The method of claim 1 which further comprises drawing said fluid through the screen to form the pad and, after the characteristic is measured, forcing the pad away from the screen by application of a relatively increased or reduced pressure on the side of the screen which does not carry the pad.

3. The method of claim 1 which further comprises maintaining the pressure on the screen side of the pad at at least two predetermined values with respect to the pressure on the opposing side of the pad, and measuring the characteristic at both said at least two predetermined pressure values.

4. The method of claim 1 wherein the measured characteristic is an electrical characteristic.

5. The method of claim 4 which further comprises forming the pad from deposited fibers and wherein the solid is at least partially fibrous.

6. The method of claim 4 which further comprises causing a pressure difference across the pad, which repeatedly alternates between peak and trough values, determining the value of said electrical characteristic at each pressure peak and trough of a continuous series comprising at least three pressure peaks, commencing at a first pressure trough and ending with a final pressure trough, and processing said values to provide an average value of said characteristic.

7. The method of claim 1 wherein the characteristic measured is streaming potential, which characteristic is determined from measurements of the potential difference between first and second electrodes located on screen and opposed sides, respectively, of said pad.

8. The method of claim 7 which further comprises determining the pad conductance, or resistance, and temperature of the fluid.

9. The method of claim 8 which further comprises determining the Zeta potential of the dispersion from measurements of the fluid's temperature, pad conductance and streaming potential.

10. A method for measuring a pressure dependent characteristic of a dispersion of a solid material in a fluid, said method comprising passing the fluid through a screen until a pad of the solid material is formed on the screen, causing a pressure difference across the pad which repeatedly alternates between peak and trough values, determining the value of said characteristic at each pressure peak and trough of a continuous series comprising at least three pressure peaks, commencing at a first pressure trough and ending with a final pressure trough, and processing said values to provide an average value of said characteristic.

11. The method of claim 10 wherein the measured characteristic is an electrical characteristic.

12. The method of claim 10, which further comprises adjusting the values of the characteristic determined at the pressure peaks in response to an average of the values of the characteristic, determined at the immediately preceding and following pressure troughs and processing the resulting adjusted values to provide a final value of said characteristic.

13. The method of claim 12, which further comprises subtracting the mean of the values of said characteristic, determined at each pair of said immediately preceding and following pressure troughs, from the value of said characteristic determined at each intermediate pressure peak, to provide an adjusted value corresponding to each pressure peak, and processing said adjusted values to provide a final value of said characteristic.

14. The method of claim 13 which further comprises determining the median of said adjusted values to provide a final value of said characteristic.

15. The method of claim 13 which further comprises rejecting the final value of said characteristic if the difference between the values of the characteristic determined at the first and last pressure troughs exceeds a predetermined value.

16. An apparatus for measuring a pressure dependent characteristic of a dispersion of a solid material in a fluid, said apparatus comprising means for passing the fluid through a sceen to form a pad of the solid material on the screen, and the means for measuring the characteristic comprises two electrodes located in the first chamber and pressure regulating means for maintaining the pressure on the screen side of the pad at a predetermined value with respect to the pressure on the opposing side of the pad during measurement of the characteristic.

17. The apparatus claim 16 further comprising a cell divided into first and second chambers by said screen, said cell arranged to allow the dispersion to enter the first chamber and a portion of the liquid to pass through the screen into the second chamber, leaving the pad of solid material on the screen, wherein the pressure regulating means is adapted to maintain the pressure in the second chamber at the predetermined value with respect to the pressure in the first chamber during measurement of the characteristic.

18. The apparatus of claim 17 wherein the pressure regulating means is adapted to maintain the pressure in the second chamber at two or more predetermined values with respect to the pressure in the first chamber.

19. The apparatus of claim 17 wherein the pressure regulating means comprises means for drawing air from and forcing air into the second chamber, at a rate sufficient to maintain the pressure in the second chamber at said predetermined value.

20. The apparatus of claim 19 wherein the pressure regulating means is adapted to draw the dispersion into the cell and fluid through the screen, to form the pad, and to force the fluid, pad and dispersion out of the cell after the characteristic has been measured.

21. The apparatus of claim 16 wherein the pressure regulating means comprises at least one differential pressure regulator, said at least one regulator arranged to provide a pressure signal corresponding to a predetermined pressure value, and means responsive to each said pressure signal for drawing air from or forcing air into the second chamber to maintain the pressure in the second chamber at said predetermined value.

22. The apparatus of claim 21 wherein the means responsive to the pressure signal comprises a volume booster, said booster arranged to regulate the output of a compressed air source and the flow of air to a vacuum reservoir.

23. The apparatus of claim 21 wherein the cross-sectional area of the screen is less than the maximum cross-sectional area of the first chamber.

24. The apparatus of claim 23 wherein the cross-sectional area of said screen is about 1/16 of said cross-sectional area of the first chamber.

25. The apparatus of claim 16 which further comprises a gauze having a mesh size of between 5 $\mu$m and 200 $\mu$m located across the first chamber, immediately adjacent to the screen.

26. An apparatus for measuring an electrical characteristic of a dispersion of a solid material in a fluid, said apparatus comprising a cell divided into first and second chambers by a screen, said screen positioned and adapted to allow the dispersion to enter the first chamber and a portion of the liquid to pass through the screen and into the second chamber, leaving a pad of the solid material on the screen, and at least one electrode for measuring said characteristic, wherein said at least one electrode is substantially flush with the wall of the first chamber.

27. The apparatus of claim 26 wherein said at least one electrode is annularly-shaped.

28. The apparatus of claim 26 wherein first and second electrodes are located in said first chamber.

29. The apparatus of claim 28 wherein said screen serves as said first electrode and said second electrode is spaced a distance apart from said screen.

30. The apparatus of claim 28 wherein said first electrode is located immediately adjacent said screen and said second electrode is spaced a distance apart from said screen.

31. The apparatus of claim 28 which further comprises computer control means in communication with the pressure regulating means and the electrodes, said computer control means adapted for controlling the pressure regulating means to regulate the ingress and egress of liquid into and out of the cell and the pressure across the pad, in addition to recording and processing an electrical characteristic measured between the electrodes, to provide a final value of said characteristic.

32. The apparatus of claim 31 wherein the computer control means is programmed to carry out a measurement of a pressure dependent characteristic of a dispension of a solid material in a fluid and to process measured values of said characteristic in order to provide a final value thereof.

33. The apparatus of claim 32 which further comprises means for measuring the temperature of dispersion passing into the cell and means for measuring the conductivity of the pad.

* * * * *